United States Patent [19]
Waldhalm

[11] 4,386,065
[45] May 31, 1983

[54] VACCINE AGAINST EAE

[75] Inventor: Donald G. Waldhalm, Caldwell, Id.

[73] Assignee: Research Corporation, New York, N.Y.

[21] Appl. No.: 233,572

[22] Filed: Feb. 11, 1981

[51] Int. Cl.³ .................... A61K 39/12; C12N 7/04
[52] U.S. Cl. ............................. 424/89; 435/235; 435/236
[58] Field of Search ............... 424/89; 435/236, 235

[56] References Cited
U.S. PATENT DOCUMENTS 4,271,146  6/1981  Seawell ........................... 424/89

OTHER PUBLICATIONS

Stokes–Chem. Abst. vol. 80 (1974) p. 143,786y.

*Primary Examiner*—Sam Rosen
*Attorney, Agent, or Firm*—Scully, Scott, Murphy & Presser

[57] ABSTRACT

A vaccine composition and method for the immunization of ewes against EAE (enzootic abortion in ewes) based upon inactivated Chlamydia sp. propagated in cell culture. The invention also relates to a method for the preparation of said vaccine and an intermediate therefor.

10 Claims, No Drawings

VACCINE AGAINST EAE

BACKGROUND OF THE INVENTION

In the 1950's it was discovered that enzootic abortion in ewes (EAE) was carried by infection of the animals with a virus strain of the Psittacosis-Lymphogranuloma group [Young et al, J.A.V.M.A., Vol. 133 (Oct. 1, 1958) p. 374] was classified as Chlamydia sp. [Becerra et al, Zbl. Bakt., I. Abt. Orig. Vol. 214, pp. 250-258 (1970)].

Earlier in the same decade, workers in the field found that the inoculation of ewes at or near breeding time with a vaccine prepared from (1) virus infected yolk sacs or (2) virus infected ovine foetal membranes was effective in reducing the incidence of EAE. The chlamydia elementary bodies were concentrated from infected chicken embroys or foetal membranes, inactivated and used to prepare the vaccine. McEwen et al, Vet. Rec., Vol. 63, p. 197 (3/17/51); McEwen et al. Vet. Rec., Vol. 66, p. 393 (7/10/54); McEwen et al. Vet. Rec., Vol. 67, p. 393 (5/21/55); McEwen et al, Vet. Rec., Vol. 68, p. 686 (10/6/56); McEwen et al, Vet. Rec. Vol. 68, p. 690 (10/6/56); Hulet et al, Am. J. Vet. Res. Vol. 26, p. 1464 (1965); Frank et al, Am. J. Vet. Res., Vol. 29, p. 1441 (1968); Meinershagen et al, Am. J. Vet. Res., Vol. 32, p. 51 (1971).

Serial passage of a virulent microorganism outside the natural host is an accepted method for selecting variants (attenuated strains) with decreased virulence. Wilson, G. S., and Miles, A. Topley and Wilson's Principles of Bacteriology, Virology, and Immunity, Williams & Wilkins, 6th edition 1975 Vol. 1, p. 412-416.

There have also been reports of successful immunizations of ewes against chlamydial abortion with chlamydial organisms attenuated by serial passage in chicken embroys. See Mitscherlich, E., The Control of Virus Abortion of Sheep, Berl-Munch. Tierarztl, Wschr. 78, Heft 5: 81-100 (1965); Nejvestic, A. and Forsek, Z., Active Immunization in the Prophylaxis of Enzootic Abortion in Ewes—I. Vet. Glasnik, 23, 6: 423-427 (1969); Schoop, G., Wachendorfer, G., Kruger-Hansen-Schoop, U., and Berger, J., Studies on a Live Vaccine for the Control of Miyagawanella Abortion in Sheep, Zbl. Vet. Med., Reihe B., 15, Heft 2: 209-223 (1968); Yilmaz, S., and Mitscherlich, E., Experiences in the Control of Ovine Enzootic Abortion with a Live Vaccine made from an Attenuated Strain of Chlamydia ovis, strain "P", Berl. Munch., Tierarztl., Wschr. 86, Heft 19: 361-366 (1973). Other reports, however, indicate that the virulence of chlamydial organisms was not diminished by serial passage in cell culture or in chicken embryos. See Becerra, V. M., Ata, F. A., and Storz, J., Studies on the Response of Ewes to Live Chlamydia Adapted to Chicken Embryos or Tissue Culture, Canad., J. Compar. Med. 40: 46-52 (1976); Becerra, V. M., and Storz, J., Tissue Culture Adaptation and Pathogenic Properties of an Ovine Chlamydial Abortion Strain, Zentbl, Vet. Med 21: 288-299 (1974); and McKercher, D. G., Robinson, E. A., Wade, E. M., Saito, J. K. and Franti, C. E., Vaccination of Cattle against Epizootic Bovine Abortion, Cornell Vet. 59: 211-226 (1969).

The cost of producing a vaccine utilizing infected yolk sac and/or ovine foetal membrane, however, is prohibitive. Moreover, the vaccine produced according to the published methods is difficult to standardize. The yolk sac and foetal membrane techniques are not only expensive but are time-consuming and inefficient. As a result, there is no commercially attractive EAE vaccine available in the United States at the present time. It is believed that immunizations against EAE are presently carried out only in Idaho utilizing locally batch-produced yolk sac or foetal membrane based vaccines. The difficulty of standardization of these vaccines, however, has led to mixed and unpredictable results.

Inasmuch as enzootic abortion in ewes (EAE) is a serious problem in the sheep-breeding industry and responsible for abortion losses in susceptible flocks as high as 30%, there is an urgent need for an economically viable vaccine and method for the active immunization of ewes against EAE.

It is an object of the present invention to provide a vaccine for the active immunization of ewes against enzootic abortion.

It is a further object of the present invention to provide a method for immunizing ewes against EAE.

It is a further object of the present invention to provide a relatively simple, efficient and economically attractive method for the preparation of a vaccine against EAE.

It is a still further object of the present invention to provide an easily standardized intermediate composition especially adapted for preparing a vaccine against EAE.

SUMMARY OF THE INVENTION

The invention is predicated on the discovery that an economically feasible and commercially attractive vaccine for the active immunization of ewes against enzootic abortion (EAE) can be prepared from Chlamydia sp. elementary bodies propagated on and isolated from cell culture. It has been found that cell culture grown Chlamydia sp. elementary bodies are more economically and efficiently produced than chicken embryo and foetal membrane derived strains. Moreover, the cell culture produced composition is more readily standardized than those produced heretofore.

DETAILED DESCRIPTION OF THE INVENTION

The invention relates to an aqueous suspension of inactivated chlamydial elementary bodies propagated on and isolated from a cell culture from which a vaccine against EAE can be formulated by dilution with a parenterally administrable carrier.

Following is a non-limiting example of a method for the preparation of the aqueous suspension:

A single strain of Chlamydia sp. isolated from an infected ovine fetus is used to prepare the suspension. The organism is propagated on cultures of mouse fibroblast L-cells (NCTC 929) either in standing monolayers, roller bottles, or suspended microcarrier cultures using 10% Eagle's Minimum Essentials Medium supplemented with 5% bovine fetal serum. A confluent monolayer (or its equivalent in a roller bottle or suspended culture) is inoculated with 1 ml of chlamydia suspension containing $1 \times 10^8$ embryo lethal doses $(ELD_{50})/0.5$ ml. The cultures are incubated at 37° C. in a $CO_2$ incubator.

Smears are prepared daily from the infected L-cells and stained by the Gimenez method. (Clark et al, Staining Procedures Used by the Biological Stain Commission, 3rd Ed. Williams & Wilkins Co., Balt. Md. 1973, p. 291). When an estimated 80-90% of the L-cells are infected, the tissue culture medium from the infected L-cells and the infected L-cells which have been detached from the growth surface with a versene-trypsin solution are combined to use as inoculum for fresh L-cell cultures. One standing monolayer (or its equivalent) is used as "seed" for 5 fresh monolayers (or equivalent) of equal size and volume. The progress of the chlamydia infection is again monitored as above.

The culture fluid and infected L-cells from standing culture flasks (or equivalents) are harvested when 80–90% of the cells are infected. The infected fluids and detached cells are pooled and centrifuged at $16,300 \times g$ for 30 minutes. The supernatent fluid is discarded and the pellet resuspended in Bovarnicks' sucrose-phosphate buffer (Bovarnicks et al, J. Bact. 1950, Vol. 59, pp. 509–22) to give a final volume equal to 1/100 of the amount harvested. A 2 ml portion of this suspension is removed for infectivity titration in 7-day-old chicken embryo. Sufficient formalin is added to the remainder to give a final concentration of 0.4% formalin. The formalin-treated suspension is stored at 37° C. for 1 week and then tested for sterility.

The suspension is again separated by centrifugation, the supernatant fluid discarded, and the pellet resuspended in phosphate buffered physiological saline containing 0.2% formalin. The final volume is adjusted (using the results of the infectivity titration) to give a concentration of chlamydial elementary bodies equivalent to $10^{8.3}$ ELD$_{50}$/0.25 ml.

It will be understood that the chlamydial strain may be obtained from any convenient source and propagated on any suitable cell culture, e.g., chicken fibroblasts, yolk sac, McCoy (human synovium), lamb fetal kidney, lamb fetal lung, lamb fetal spleen, FAM (human amnion), HEP-2 (human laryngeal tumor, lamb testicle, He La, Sirc (rabbit cornea), green lizard liver, etc., cells.

It will also be apparent that any suitable killing agent can be utilized for the purpose of inactivating the chlamydia organisms, e.g., formalin, ultraviolet irradiation, thermal (56° C. for 5 or more minutes), phenol, repeated freezing and thawing, beta-propiolactone, acetone, ether, acetone-ether mixtures, etc.

The propagation may be continued until there is present in the final suspension an amount of chlamydial elementary bodies in the range of from $10^6$ to $10^9$ ELD$_{50}$/0.25 ml.

A vaccine in unit dosage form suitable for immunization against EAE may be formulated by diluting the above aqueous suspension with an equal volume of a physiologically acceptable and parenterally administrable carrier. For example, an equal volume of oil adjuvant (4 parts light mineral oil and 1 part lanolin) may be added to the suspension prepared above in a mechanical blender operated at low speed. When the addition of the adjuvant is complete, the resulting mixture is homogenized, bottled, and stored for use.

The vaccine is administered by subcutaneous injection of a single 1 ml dose at or near breeding time, it being understood that a suitable dose is one containing from about $2 \times 10^6$ to about $2 \times 10^9$ ELD$_{50}$/ml.

The resulting vaccine is much less expensive to prepare, is more readily standardized and yields a more enhanced degree of immunization against EAE than the previously proposed vaccines derived from chicken embryos (yolk sac) and ovine foetal membranes.

In order to demonstrate the value and effectiveness of the vaccine of the present invention, an attempt was made to attenuate a chlamydial strain by serial passage in chicken embryos and prepare a vaccine therefrom. The procedure employed was as follows:

A single strain of *Chlamydia psittaci* (Ark 2) was used in the experiment. The test organism was isolated from an aborted lamb and was cultured by serial passages in seven-day-old CE. The chlamydia for inoculation of ewes in Lot 2 were passed in CE 7 times at 37 C and 10 times at 40 C. For Lots 1 and 3, the inoculums were prepared from chlamydia cultured in CE at 37 C for the number of passages indicated (Table 1). Lot 3 served as a control in which the ewes were inoculated with a virulent strain of chlamydia. Lot 4 was not inoculated and served as a normal control. Preparation of inoculums for sheep and their CE infectivity determinations were performed according to the methods described in Reed, L. J. and Muench, H., A Simple Method of Estimating Fifty Percent Endpoints, Am. J. Hyg. 26: 493–497 (1938); Storz, J., Chlamydia and Chlamydia-Induced Diseases, Chas. C. Thomas, 1971, p. 154; and Waldhalm, D. G., Frank, F. W., Meinershagen, W. A., Philip, R. N., and Thomas, L. A., Lamb Performance of Ewes Inoculated with Chlamydia sp. Before and After Breeding, Am. J. Vet. Rest., 32: 809–811 (1971). The inoculums given ewes in Lots 1 and 2 contained $10^{8.48}$ and $10^{3.46}$ 50% embryo lethal endpoint units (ELD$_{50}$), respectively. Primiparous ewes were inoculated intramuscularly with 1 ml of chlamydia suspension at approximately the 100th day of gestation.

Liver and stomach contents from aborted fetuses and lambs which died in less than 24 hours after birth were cultured for *Campylobacter (Vibrio) fetus* and other pathogenic bacteria. Stained [Stamp, J. T., McEwen, A. D., Watt, J. A. A., and Nisbet, D. L., Enzootic Abortion in Ewes, I, Transmission of the Disease, Vet. Rec. 62: 251 (1950)] impression smears from placentas, vaginal discharges, and the skin surfaces of aborted fetuses were examined for the presence of chlamydia.

The results were summarized (Table I). No pathogenic bacteria were isolated from aborted fetuses or from weak lambs. The ewes in Lot 3 had the highest percentage of abortion (67%), but there was no statistically significant difference between any two of the lots ($P > 0.5$).

The results of the present study indicate that serial passage of *Chlamydia psittaci* strain (Ark 2) in CE including passages at high incubation temperature did not affect the pathogenicity of the organism for pregnant ewes. The results are in agreement with reports of other attempts to modify the virulence of chlamydia, and do not substantiate the reports of successful immunization of ewes with live chlamydia that had been subjected to serial passage in CE.

TABLE I

Pathogenicity of *Chlamydia psittaci* (strain Ark 2) in Pregnant Ewes.

| Lot No. | No. of Ewes | Inoculum Treatment | Inoculum Infectivity (ELD$_{50}$) | Ewes with Live Lambs | Ewes with Weak Lambs+ or Abortion | Number of Placentas Examined | Ewes with Infected Placentas |
|---|---|---|---|---|---|---|---|
| 1 | 12 | 110 CE passages* | $10^{8.48}$ | 5 | 7 | 6 | 6 |
| 2 | 13 | 7 CE passages | $10^{8.46}$ | 9 | 4 | 11 | 8 |

TABLE I-continued

| Lot No. | No. of Ewes | Inoculum Treatment | Inoculum Infectivity (ELD$_{50}$) | Ewes with Live Lambs | Ewes with Weak Lambs+ or Abortion | Number of Placentas Examined | Ewes with Infected Placentas |
|---|---|---|---|---|---|---|---|
| | | at 37 C. plus 10 CE passages at 40 C. | | | | | |
| 3 | 12 | 8 CE passages | ND** | 4 | 8 | 11 | 10 |
| 4 | 14 | None (Normal control) | — | 14 | 0 | 2 | 0 |

+Born alive but died within 24 hours.
*Embryos were incubated at 37 C. except as noted.
**Not determined.

A test was conducted wherein cell culture propagated vaccine was compared with chicken embryo propagated vaccine. The two vaccines contained equal amounts of inactivated chlamydia organisms and were similar in all respects except for the mode of propagation.

Eighty-three yearling ewes were selected from a commercial herd on the basis of low antibody levels against chlamydia antigen. The antibody levels were determined by enzyme-linked immunosorbent assay (ELISA). The ewes were ear tagged for identification and kept in a single group until the time of challenge inoculation.

Two days before breeding was begun, 50 randomly selected ewes were vaccinated: 25 received cell culture origin vaccine and 25 received chicken embryo origin vaccine. Vaccines were administered in 1 ml doses subcutaneously. The remaining ewes were not vaccinated.

Blood samples for serology were collected at the time of vaccination and on post vaccination days 14, 28, 100, 107 and 114. Antibody concentrations were determined by ELISA.

On post vaccination day 100 the ewes were divided into separate groups as shown in Table 2. Each ewe in the vaccinated groups and 25 nonvaccinated ewes were inoculated orally with 5 ml of a suspension of live, virulent *Chlamydia psittaci* containing $10^{8.3}$ ELD$_{50}$/05 ml in sucrose phosphate buffer.

TABLE 2

Comparison of vaccine prepared from Chlamydia grown either in chicken embryos of L-cell monolayers

| Group | No. of Ewes | Treatment | Challenge Inoculum |
|---|---|---|---|
| 1 | 25 | cell culture origin vaccine | virulent *Chlamydia psittaci* |
| 2 | 25 | chicken embryo origin vaccine | virulent *Chlamydia psittaci* |
| 3 | 25 | none (infected control) | virulent *Chlamydia psittaci* |
| 4 | 25 | none | none |

TABLE 2-continued

Comparison of vaccine prepared from Chlamydia grown either in chicken embryos of L-cell monolayers

| Group | No. of Ewes | Treatment | Challenge Inoculum |
|---|---|---|---|
| | | (normal control) | |

Aborted fetuses and associated membranes were examined microscopically and by bacteriologic culture to ascertain the cause of abortion. In all cases *Chlamydia psittaci* was determined to be the cause.

The relative efficacies of the two vaccines can be judged from the lambing performances of the various groups (Table 3) and from the antibody responses (in terms of absorbencies) elicited by the two preparations (Table 4).

TABLE 3

| Group | Treatment | Lambing performance | | |
|---|---|---|---|---|
| | | No. of Pregnant Ewes | No. of Ewes with Abortions or Weak Lambs* | No. of Infected Placentas/ No. Examined |
| 1 | cell culture vaccine | 22 | 1$^a$ | 0/12$^a$ |
| 2 | chick embryo vaccine | 25 | 2$^a$ | 0/13$^a$ |
| 3 | nonvaccinated challenged | 23 | 8$^b$ | 6/12$^b$ |
| 4 | normal control | 8 | 0$^a$ | 0/7$^a$ |

*Weak Lamb = died in 48 hours or less
$^{a,b}$Values between treatments with different superscripts differ (P > 0.03) significantly.

TABLE 4

| | | Mean ELISA Absorbencies ($\overline{X} \pm S.D.$) | | | | | |
|---|---|---|---|---|---|---|---|
| | | Days Post Vaccination: | | | | | |
| Group | Treatment | 0 | 14 | 28 | 100* | 107 | 114 |
| 1 | cell culture vaccine | 0.15 ± .11 | 0.28 ± .15 | 0.50 ± .24 | 0.48 ± .17 | 0.44 ± .21 | 0.55 ± .18 |
| 2 | chick embryo vaccine | 0.16 ± .14 | 0.31 ± .24 | 0.43 ± .19 | 0.34 ± .17 | 0.33 ± .14 | 0.40 ± .13 |
| 3 | nonvaccinated challenged | 0.14 ± .09 | 0.16 ± .12 | 0.16 ± .12 | 0.14 ± .10 | 0.15 ± .09 | 0.44 ± .19 |
| 4 | normal control | 0.17 ± .14 | 0.17 ± .10 | 0.20 ± .11 | 0.14 ± .09 | 0.14 ± .10 | 0.13 ± .10 |

*Day of challenge

Both vaccines gave significant protection against abortion and weak lambs and both elicited an antibody response measurably greater than the controls. These results show further, in terms both of protection against lamb mortality and of measured antibody response, that the cell culture grown vaccine elicited a better response than the chicken embryo propagated product. This is especially evident in the greater average absorbencies shown in Group 1 from the 28th post vaccination day until the end of the study at day 114.

I claim:

1. A composition especially adapted for the formulation of a vaccine in unit dosage form for immunization against enzootic abortion in ewes comprising an aqueous suspension containing $10^6$ to $10^9$ $ELD_{50}/0.25$ ml of inactivated chlamydial elementary bodies prepared from chlamydial organisms propagated in cell culture.

2. The composition of claim 1 comprising an aqueous suspension of formalin-inactivated chlamydial elementary bodies prepared from chlamydial organisms propagated in cell cultures.

3. A vaccine in unit dosage form for immunization against enzootic abortion in ewes comprising an immunizing amount of inactivated chlamydial elementary bodies in the range of from $2 \times 10^6$ to $2 \times 10^9$ $ELD_{50}/ml$ prepared from chlamydial organisms propagated in cell culture and a parenterally administrable liquid carrier therefor.

4. The vaccine of claim 3 comprising an admixture of an aqueous suspension of formalin-inactivated chlamydial elementary bodies prepared from chlamydial organisms propagated in cell culture and an equal amount of oil adjuvant.

5. The vaccine of claim 4 wherein said oil adjuvant comprises a mixture of light mineral oil and lanolin.

6. A method for immunizing ewes against enzootic abortion comprising parenterally adminstering to an ewe the vaccine of claim 3.

7. The method of claim 6 wherein said vaccine is administered subcutaneously.

8. The method of claim 7 wherein said vaccine is administered at or near the time for breeding said ewe.

9. A method for the preparation of a vaccine composition for immunization against enzootic abortion in ewes comprising propagating chlamydial organisms in cell culture, inactivating said chlamydial organisms to produce inactivated chlamydial elementary bodies and combining from $2 \times 10^6$ to $2 \times 10^9$ $ELD_{50}/ml$ of said inactivated chlamydial elementary bodies with a parenterally administrable carrier therefor.

10. The method of claim 9 comprising the propagation of Chlamydia sp. in cell culture, inactivating said propagated Chlamydia sp. with formalin to yield an aqueous suspension of said inactivated chlamydial elementary bodies and admixing said aqueous suspension with an equal amount of a parenterally administrable carrier.

* * * * *

UNITED STATES PATENT AND TRADEMARK OFFICE
CERTIFICATE OF CORRECTION

PATENT NO. : 4,386,065
DATED : May 31, 1983
INVENTOR(S) : Donald G. Waldhalm

It is certified that error appears in the above-identified patent and that said Letters Patent are hereby corrected as shown below:

Col. 1, line 17, "embroys" should read --embryos--

Col. 1, line 36, "embroys" should read --embryos--

*Signed and Sealed this*

*Twenty-fifth* Day of *October 1983*

[SEAL]

*Attest:*

GERALD J. MOSSINGHOFF

*Attesting Officer*  *Commissioner of Patents and Trademarks*